US00PP27384P3

(12) United States Plant Patent
MacGregor et al.

(10) Patent No.: US PP27,384 P3
(45) Date of Patent: Nov. 15, 2016

(54) ***ANEMONE* PLANT NAMED 'MACANE004'**

(50) Latin Name: ***Anemone* hybrid**
Varietal Denomination: MACANE004

(71) Applicants: Alasdair MacGregor, Kirkcudbright (GB); Elizabeth MacGregor, Kirkcudbright (GB)

(72) Inventors: Alasdair MacGregor, Kirkcudbright (GB); Elizabeth MacGregor, Kirkcudbright (GB)

( * ) Notice: Subject to any disclaimer, the term of this patent is extended or adjusted under 35 U.S.C. 154(b) by 127 days.

(21) Appl. No.: 14/544,129

(22) Filed: Nov. 28, 2014

(65) Prior Publication Data

US 2016/0157405 P1 Jun. 2, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP23,132 P2 * 10/2012 MacGregor et al. ..... Plt./263.1

* cited by examiner

*Primary Examiner* — Anne Grunberg
(74) *Attorney, Agent, or Firm* — Cassandra Bright

(57) ABSTRACT

A distinct new cultivar of *Anemone* plant named 'MACANE004', characterized by a short, compact plant habit and semi-double, white and violet colored flowers. The new cultivar is an *Anemone* typically suited for ornamental container and landscape use.

2 Drawing Sheets

Figure 1:
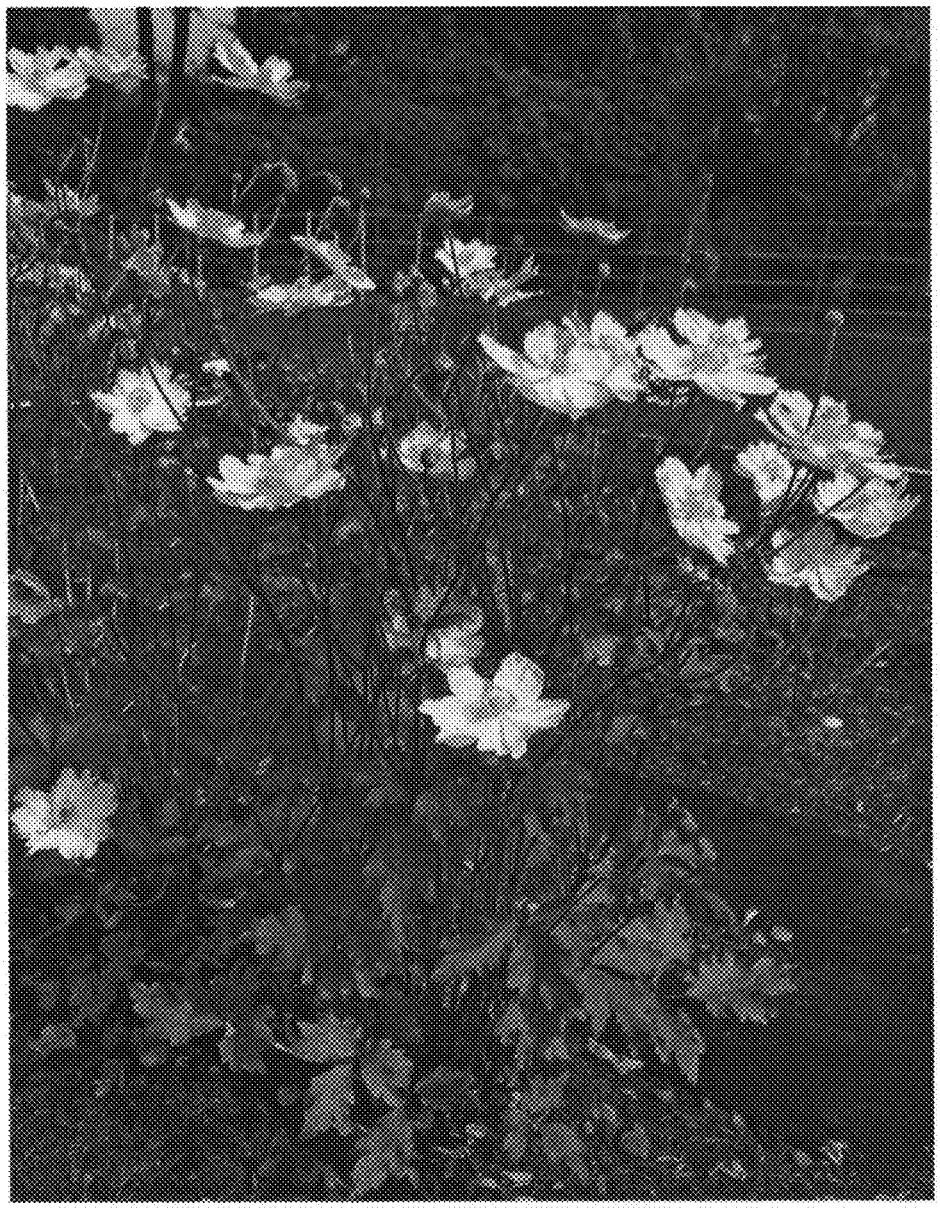

Latin name of the genus and species: *Anemone* hybrid.
Variety denomination: 'MACANE004'.

BACKGROUND OF THE INVENTION

The new *Anemone* was discovered by the inventors, Elizabeth and Alasdair MacGregor, as part of a breeding program, using *Anemone* hybrids as parents. The seed parent is *Anemone* hybrid 'Pamina' which was crossed with the unpatented *Anemone* hybrid 'Rosenschale'. The cross was made in 2006, and the selection of the new variety made during 2008 at a commercial nursery, in Kirkcudbright, Scotland.

Asexual reproduction by tissue culture has been undertaken in 2008, by at a commercial laboratory in the Netherlands. Plants produced have proved to be stable and reproduced true to type in successive generations.

SUMMARY OF THE INVENTION

The cultivar 'MACANE004' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MACANE004'. These characteristics in combination distinguish 'MACANE004' as a new and distinct *Anemone* cultivar:

1. Semi-double, white flowers, with a violet-blue under side coloration to flower.
2. Compact plants, with a height of 30 to 40 cm.

PARENTAL COMPARISON

Plants of the new cultivar 'MACANE004' are similar to the seed parent in most horticultural characteristics. However, plants of 'MACANE004' differ in that they produce semi-double two toned flowers, whereas the seed parent produces single, pure white flowers. Flowers of the new variety are also larger in diameter than flowers of the seed parent.

Plants of the new cultivar 'MACANE004' are similar to the pollen parent in most horticultural characteristics. However, plants of 'MACANE004' differ in that they produce semi-double two toned flowers, whereas the pollen parent produces single, deep pink flowers.

COMMERCIAL COMPARISON

Plants of the new cultivar 'MACANE004' are similar to the known commercial variety, *Anemone hybrida* 'Whirlwind', unpatented, in some horticultural characteristics. However, plants of 'MACANE004' differ in the following:

1. Plants of 'MACANE004' flower at a height of approximately 45 cm, compared to 80 to 90 cm plants of 'Whirlwind'.
2. 'MACANE004' produces larger flowers.
3. Plant habit of the new variety is clump forming, whereas 'Whirlwind' plants are trailing/spreading.
4. Petals of the new variety are colored Violet-Blue on the underside, compared to the white underside petal coloration of 'Whirlwind'.

Plants of the new cultivar 'MACANE004' are similar to the known commercial variety, *Anemone multifida*

'Macane001' U.S. Plant Pat. No. 23,132 in some horticultural characteristics. However, plants of 'MACANE004' differ in that they are on average 15 cm shorter. Flowers of the 'MACANE004' are larger with different color shading than 'Macane001'. Additionally, the new variety produces different foliage than 'Macane001'.

BRIEF DESCRIPTION OF THE PHOTOGRAPHS

The accompanying photograph in FIG. 1 illustrates in full color a typical plants of 'MACANE004' grown outdoors in a garden in Kirkcudbright, Scotland. This plant is approximately 15 months old.

Figure 2:
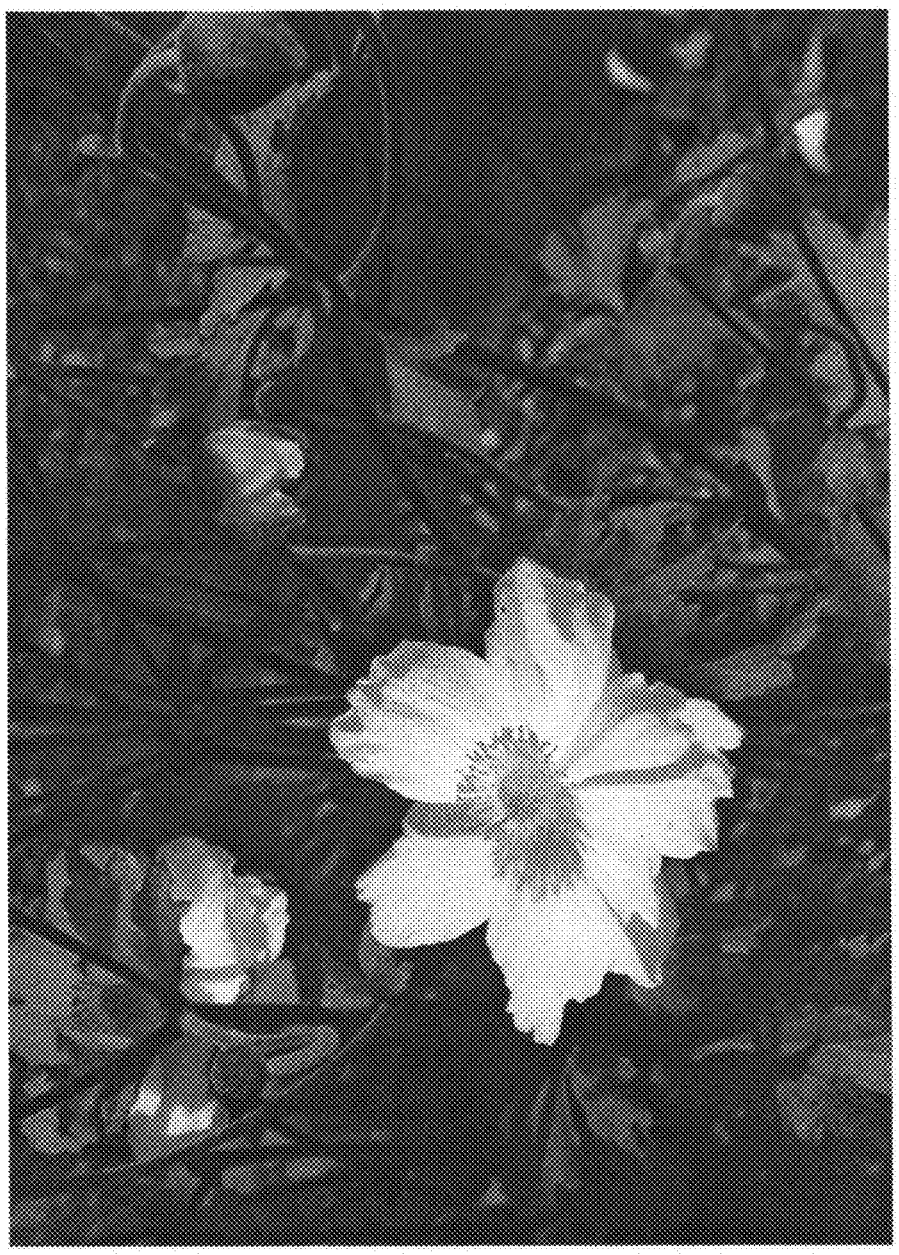

FIG. 2 illustrates a close up of the flower and flower bud.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'MACANE004' plants grown outdoors in Kirkcudbright, Scotland at a commercial nursery. The growing temperature ranged from 0° C. to 12° C. at night to 8° C. to 22° C. during the day. During the winter period December to March, plants were sheltered in a large poly-tunnel with day temperatures ranging from 5° C. to 18° C., and night temperatures ranging from −5° C. to 8° C. No artificial light, photoperiodic treatments or chemical treatments were given to the plants: Measurements and numerical values represent averages of typical flowering types.

Botanical classification: *Anemone* hybrid 'MACANE004'.

Age of the plant described: Approximately 15 months.

Container size of the plant described: 2 liter commercial container.

PROPAGATION

Time to produce a flowering plant from root-cutting: Nine to twelve months.

Root description: Fibrous, reddish-brown (not RHS identified) in color.

Rooting habit: Dense, freely branching.

PLANT

Growth habit: Upright.

Pot size of plant described: 2 liter circular pot (14 cm).

Height: 34.8 cm.

Plant spread: 39.8 cm.

Growth rate: Moderate.

Branching characteristics: No lateral branches, flowering stems grow from a basal rosette.

Length of primary lateral branches: No lateral branches present, basal branching.

FOLIAGE

Leaf:

*Arrangement*.—Basal rosette.

Leaflets:

*Shape*.—Trifoliate, broad ovate in outline.

*Quantity*.—Approximately 5 per basal rosette.

*Average length*.—12.0 cm.

*Average width*.—11.5 cm.

Individual leaf blades:

*Shape of blade*.—Ovate.

*Apex*.—Short apiculate.

*Base*.—Acute to short attenuate.

*Margin*.—Biserrate.

*Texture of top surface*.—Very slightly glossy.

*Pubescence*.—Upper side sparsely covered with short adpressed hairs, average length: 0.05 cm, coloured near RHS NN155D, main veins and secondary veins on under side moderately covered with short adpressed hairs, average length: 0.05 cm, coloured near RHS 157D.

*Aspect*.—Leaf blades in an average angle of 80° to petiole.

*Color*.—Young foliage upper side: Near RHS 143A. Young foliage under side: In between near RHS 143A and 146B. Mature foliage upper side: Near RHS N137B. Mature foliage under side: Near RHS 147C.

*Venation*.—Type: Pinnate. Venation color upper side: Near RHS 144A. Venation color under side: Near RHS 148C.

*Petiole*.—Length: 19.8 cm. Diameter 0.2 cm. Color: Near RHS 177A, under side near RHS 144A, petiole heavily tinged tinged near RHS N79A towards the base. Texture: Moderately covered with short hairs, average length: 0.1 cm, coloured near RHS NN155D.

*Stipule description* (*if present*).—Length: 2.1 cm. Diameter: 0.5 cm. Color: Near RHS 145C to 145D Texture: Moderately covered with short hairs, average length: 0.2 cm, coloured near RHS N79D.

FLOWER

Natural flowering season: Summer.

Days to flowering from rooted cutting: 9-12 months.

Inflorescence and flower type and habit: Inflorescence a terminal corymb, individual flowers rotate, single.

Rate of flower opening: 14 to 21 days from bud to fully opened flower.

Flower longevity on plant: Approximately one week.

Persistent or self-cleaning: Self-cleaning.

Bud:

*Shape*.—Broad ovate.

*Length*.—1.0 cm.

*Diameter*.—0.9 cm.

*Color*.—In between near RHS 145A and 147D.

Flower size:

*Diameter*.—6.9 cm.

*Depth*.—2.7 cm.

*Aspect*.—Upright to outward.

Tepals: No separate petals and sepals present, these floral structures are referred to as "Tepals" here.

*Quantity*.—7.

*Arrangement*.—Rotate.

*Length*.—3.6 cm.

*Width*.—2.4 cm.

*Shape*.—Broad elliptic to obovate.

*Apex*.—Obtuse to broad acute.

*Base*.—Broad cuneate.

*Margin*.—Entire.

*Texture, upper and lower surfaces*.—Glabrous, matte, slightly velvety.

*Color*.—When opening, upper surface: Near RHS 155A, tinged Violet 85C and 85D. When opening, lower surface: Near RHS Purple-Violet N82C and Violet 84A. Fully opened, upper surface: Near RHS NN155D. Fully opened, lower surface: Near RHS NN155C, slightly tinged Violet 85C.

Bracts (if present): No bracts present.

Longest peduncles:

*Length*.—25.4 cm.

*Diameter*.—0.35 cm.

*Angle*.—About 90° to basal rosette.

*Strength*.—Moderately strong.

*Texture*.—Slightly glossy, densely covered with short soft hairs, average length: 0.1 cm, coloured near RHS NN155D.

*Color*.—Near RHS 146B, coloured N186C to 187A towards the base.

Shortest peduncles:

*Length*.—7.0 cm.

*Diameter*.—0.2 cm.

*Angle*.—About 30° to the peduncle.

*Strength*.—Moderately strong.

*Texture*.—Slightly glossy, very densely covered with short soft hairs, average length: 0.1 cm, coloured near RHS NN155D.

*Color*.—Near RHS 147D.

Fragrance: No fragrance.

REPRODUCTIVE ORGANS

Stamens:

*Number*.—Average: 250.

Anthers:

*Shape*.—Narrow kidney-shaped to oblong.

*Length*.—Approximately 0.2 cm.

*Color*.—Near RHS Yellow-Orange 14A.

*Pollen*.—Color: Near RHS Yellow-Orange 14A. Quantity: Very low.

Pistil:

*Number*.—Average: 250.

*Length*.—0.25 cm.

*Style*.—Length: 0.2 cm. Color: Near RHS Yellow-Green 144A and 144B.

*Stigma*.—Shape: Pointed. Color: Near RHS Yellow-Green 144C. Ovary Color: Near RHS Yellow-Green 144C.

OTHER CHARACTERISTICS

Seed/fruit: No seeds/fruits detected to date.

Temperature tolerance: Plants of the new *Anemone* h are hardy to at least USDA Zone 6.

Diseases and pests: Neither resistance nor susceptibility to normal diseases and pests of *Anemone* has been observed.

What is claimed is:

1. A new and distinct cultivar of *Anemone* hybrid plant named 'MACANE004' as herein illustrated and described.

* * * * *